United States Patent
Imran et al.

(10) Patent No.: US 10,130,514 B2
(45) Date of Patent: Nov. 20, 2018

(54) SYSTEM AND METHOD FOR DELIVERY OF A THERAPEUTIC AGENT TO THE INNER EAR

(71) Applicant: InCube Labs, LLC, San Jose, CA (US)

(72) Inventors: Mir Imran, Los Altos Hills, CA (US); Joel Harris, Mountain View, CA (US)

(73) Assignee: InCube Labs, LLC, San Jose, CA (US)

( * ) Notice: Subject to any disclaimer, the term of this patent is extended or adjusted under 35 U.S.C. 154(b) by 208 days.

(21) Appl. No.: 13/627,346

(22) Filed: Sep. 26, 2012

(65) Prior Publication Data
US 2013/0085476 A1 Apr. 4, 2013

Related U.S. Application Data

(60) Provisional application No. 61/626,439, filed on Sep. 26, 2011.

(51) Int. Cl.
*A61F 11/00* (2006.01)
*A61K 9/00* (2006.01)

(52) U.S. Cl.
CPC ............ *A61F 11/00* (2013.01); *A61F 11/004* (2013.01); *A61K 9/0046* (2013.01)

(58) Field of Classification Search
CPC ............ A61M 5/1689; A61M 5/31568; A61M 25/0108; A61M 25/0082; A61M 25/0084;
(Continued)

(56) References Cited

U.S. PATENT DOCUMENTS 1,533,753 A * 4/1925 Munch .......................... 604/207
4,578,061 A * 3/1986 Lemelson ............ A61N 5/1014
604/170.01
(Continued)

OTHER PUBLICATIONS

Cancer.org—"Dexamethasone", Internet, last edited Oct. 26, 2009; retrieved Feb. 18, 2015 at http://www.cancer.org/treatment/treatmentsandsideeffects/guidetocancerdrugs/dexamethasone.*

*Primary Examiner* — Nathan R Price
*Assistant Examiner* — Justin L Zamory
(74) *Attorney, Agent, or Firm* — Wilson Sonsini Goodrich and Rosati, P.C.

(57) ABSTRACT

Embodiments of the invention provide systems and methods for delivering therapeutic compositions to the inner-ear to treat inner-ear disorders. An embodiment of such a system comprises a sheath for insertion into the auditory canal and a cannula which can be inserted through the sheath. The cannula can include a tip for piercing the tympanic membrane and delivering the composition to an inner-ear tissue surface. The system may also include a therapeutic composition comprising a therapeutic agent and a thixotropic material which allows the composition to be delivered (e.g., by injection) through the cannula in liquid form and transition to gel-form once delivered to the tissue surface. A method for using the system comprises introducing the sheath into the ear, introducing the cannula through the sheath to pierce the tympanic membrane and position the tip adjacent an inner-ear tissue surface; and delivering the composition through the cannula to adhere to the tissue surface.

22 Claims, 12 Drawing Sheets

(58) Field of Classification Search
CPC .. A61M 2025/0089; A61M 2210/0662; A61M 2210/0668; A61M 2210/0675; A61F 11/00; A61F 11/004; A61K 9/0046; B01L 3/0272; B01L 2200/061; A61J 2200/76
See application file for complete search history.

(56) References Cited

U.S. PATENT DOCUMENTS

| | | | |
|---|---|---|---|
| 4,877,585 A * | 10/1989 | Perlman | B01L 3/021 422/516 |
| 5,212,162 A | 5/1993 | Missel et al. | |
| 6,796,976 B1 * | 9/2004 | Chin | A61M 25/01 604/164.07 |
| 7,016,504 B1 | 3/2006 | Shennib | |
| 7,351,246 B2 * | 4/2008 | Epley | A61F 11/00 604/275 |
| 7,820,202 B2 | 10/2010 | Bodmeier | |
| 8,190,252 B2 | 5/2012 | Imran | |
| 2003/0191064 A1 * | 10/2003 | Kopke | A61K 31/05 514/266.1 |
| 2006/0193877 A1 | 8/2006 | Tengler et al. | |
| 2007/0100318 A1 | 5/2007 | Seward et al. | |
| 2009/0246255 A1 * | 10/2009 | Meyer | A61K 9/0046 424/437 |
| 2010/0022661 A1 * | 1/2010 | Lichter | A61K 9/0046 514/772.1 |
| 2011/0166060 A1 * | 7/2011 | Simons | A61K 9/0046 514/2.8 |

\* cited by examiner

SYSTEM AND METHOD FOR DELIVERY OF A THERAPEUTIC AGENT TO THE INNER EAR

CROSS-REFERENCE TO RELATED APPLICATIONS

This application claims benefit of priority to Provisional U.S. Patent Application No. 61/626,439, entitled "Device and Method for Delivery of a Therapeutic Agent to the Inner Ear", filed Sep. 26, 2011; the aforementioned priority application being hereby incorporated by reference for all purposes.

BACKGROUND OF THE INVENTION

Field of the Invention

Embodiments described herein relate to a system and method for delivery of therapeutic agents to various locations in the body such as the head. More specifically, embodiments described herein relate to a system and method for delivery of a therapeutic composition comprising a therapeutic agent to the ear. Still more specifically, embodiments described herein relate to a system and method for delivery of a therapeutic composition to the inner ear.

There are many disorders of the inner ear which cannot be efficiently treated via systemic drug delivery. This is because of a blood-cochlear barrier, similar to the blood-brain barrier. The blood-cochlear barrier limits the size and concentration of molecules which are able to leave the circulation and gain access to the inner ear.

Techniques have been developed, however, to improve drug delivery to the inner ear. For example, intratympanic approaches deliver drugs to the middle ear, which then permeate through tissue for access to the inner ear. Also, intracochlear methods are available by which drugs are directly inserted into the inner ear. Despite the existence of current intratympanic and intracochlear methods, there is still a need for improved techniques for inner ear drug delivery.

BRIEF SUMMARY OF THE INVENTION

Embodiments of the invention provide a system and method for delivery of a therapeutic agent to various locations in the body. Many embodiments provide a system and method for delivery of a therapeutic agents to the ear. Particular embodiments provide a system and method for delivery of one or more therapeutic agents to the inner ear for treatment of various disorders of the inner ear. Treatment of any type of inner ear disorder is contemplated as is treatment of other disorders such as various neural disorders. In many embodiments, the therapeutic agent is delivered in the form of a therapeutic agent composition (herein referred to as therapeutic composition) comprising the therapeutic agent and one or more excipients. In these and related embodiments, the therapeutic composition can be configured to be delivered in a liquid form (also described herein as a liquid state) and then once delivered, transition to a gel form (also described herein as a gel state).

In one embodiment, the invention provides a system for delivering a therapeutic composition to the inner ear, the system comprising a delivery sheath and a delivery cannula. The sheath is sized and otherwise configured to be inserted into the auditory canal and includes a lumen for advancement of the cannula. The cannula includes a lumen and is sized and otherwise configured to be advanced through the sheath into the inner ear and have its distal tip be positioned adjacent the round window membrane or other structure in the inner ear to deliver the therapeutic composition though the lumen to that location. One or both of the sheath and the cannula can include markers visible under fluoroscopy, ultrasound or other medical imaging modality to facilitate positioning of the sheath in the auditory canal and the cannula in the inner ear, including positioning of the distal tip of the cannula adjacent the round window. In particular embodiments, the distal tip of the cannula can include a sized marker, described herein as a gauge marker which the physician can use as a gauge to size the diameter or other major dimension of a drop or other shape of therapeutic composition placed on the round window membrane or other location in the inner ear. In use, such a gauge facilitates placement of a drop (or other shape) of a therapeutic composition on the surface of the round window such that the drop does not interfere with the patient's hearing including not significantly affecting the function of the round window and/or not significantly blocking the patient's Eustachian tube. Other means for determining the size of the drop placed on the round window membrane are also contemplated including the use of various sensors placed on the cannula distal tip. In addition to size, other means for assessing the amount of therapeutic composition placed on the round window membrane, such as use of various metered pumps and/or syringes to control the volume and/or mass of therapeutic composition placed on round window membrane or other location in the inner ear.

Typically, the distal tip of the cannula is configured to be able to penetrate the tympanic membrane and can have a pointed shape for doing so. In many embodiments, the distal of the cannula is also configured to be substantially atraumatic to the round window membrane. In particular embodiments this can be achieved by fabricating at least a portion of the distal tip from a material such as a hydrogel, which swells in the presence of fluid in the ear to then transform a tissue penetrating shape of the distal tip into a shape which is non-tissue penetrating and otherwise atraumatic to the round window membrane. Other means for converting cannula distal tip into a non-tissue penetrating form after penetrating the tympanic membrane such as configuring the tip to flair out or evert, or flair in or invert after penetration of the tympanic membrane.

Many embodiments of the invention also provide a therapeutic composition (also described herein as a therapeutic formulation) for treatment of a particular inner disorder of the inner in ear for delivery through the cannula. The therapeutic composition comprises the therapeutic agent and one or more excipients (e.g., carriers, preservatives, etc.) and can be in a liquid or gel form or combinations thereof. According to one or more embodiments, the composition can comprise a thixotropic material which allows the therapeutic composition to be delivered (e.g., by injection) through the cannula in a substantially liquid form (also described herein as a liquid state) and then, once positioned at the delivery site, increase in viscosity sufficiently to stay adhered to a tissue surface at the delivery site, such as the round window membrane for an extended period of time. Typically, the composition will increase in viscosity to assume a gel state as described above and elsewhere herein. In use, such embodiments allow the delivered therapeutic formulation to function as drug reservoir or depot which delivers therapeutic agent to the inner ear for an extended period of time by diffusion of the therapeutic agent across the round window, and/or outward diffusion/elution of the therapeutic agent to the fluid bathing the round window. The amount of therapeutic agent in the composition and other properties of the composition in its gel or other higher viscosity state can be configured to have the composition deliver therapeutically effective amounts of the therapeutic agent over a period of hours or even days. Such properties can include, for example, viscosity, molecular weight, amount of cross linking, charge, etc.

Still other embodiments of the invention provide methods for delivery of a therapeutic agents to treat disorders of the inner ear. Such disorders can without limitation, noise induced hearing loss, cisplatin ototoxicity, radiation ototoxicity, antibiotic induced, ototoxicity sudden sensorineural hearing loss, surgical trauma, and autoimmune inner ear disease. An exemplary embodiment of such a method comprise introducing a delivery sheath through the auditory canal and adjacent to the tympanic membrane. Then, a cannula including a lumen is introduced through the delivery sheath until it pierces the tympanic membrane and continues until the distal tip of the cannula is adjacent to a tissue surface in the inner such as the round window membrane. A therapeutic composition is introduced through the cannula until a disorder-treating effective amount of the therapeutic composition is delivered to the round window membrane or other location in the inner ear. In some embodiments of the aforementioned method, the therapeutic composition comprises a thixotropic material which allows the therapeutic composition to covert from a semi solid or gel state into a liquid while the therapeutic composition is introduced through the cannula and then transition back to the semi-solid or gel state once delivered to the desired delivery site, for example, the surface of the round window membrane so as to adhere to the membrane or other delivery site surface in the inner ear. In use, such embodiments provide for the ability to use the adhered gel as a depot or reservoir for the long term delivery of therapeutic to various location in the inner are by having the therapeutic agent diffuse/elute out of the gel which remains in place over a prolonged period. These and other features and embodiments are described in detail in the body of specification.

BRIEF DESCRIPTION OF THE DRAWINGS

FIG. 8*a* illustrates the distal tip in its tissue penetrating form; FIG. 8*b*, illustrates an intermediate stage of transformation of the distal; and FIG. 8*c* illustrates the completed transformed of the distal tip to its atraumatic non-tissue penetrating form.

FIG. 10*a* illustrates drop size configured not to interfere with the function of the round window membrane; FIG. 10*a* illustrates drop size configured not to block the Eustachian tube; and FIG. 10*c* illustrate use of an embodiment of the marker gauge to control drop size.

DETAILED DESCRIPTION OF THE INVENTION

Figure 1:
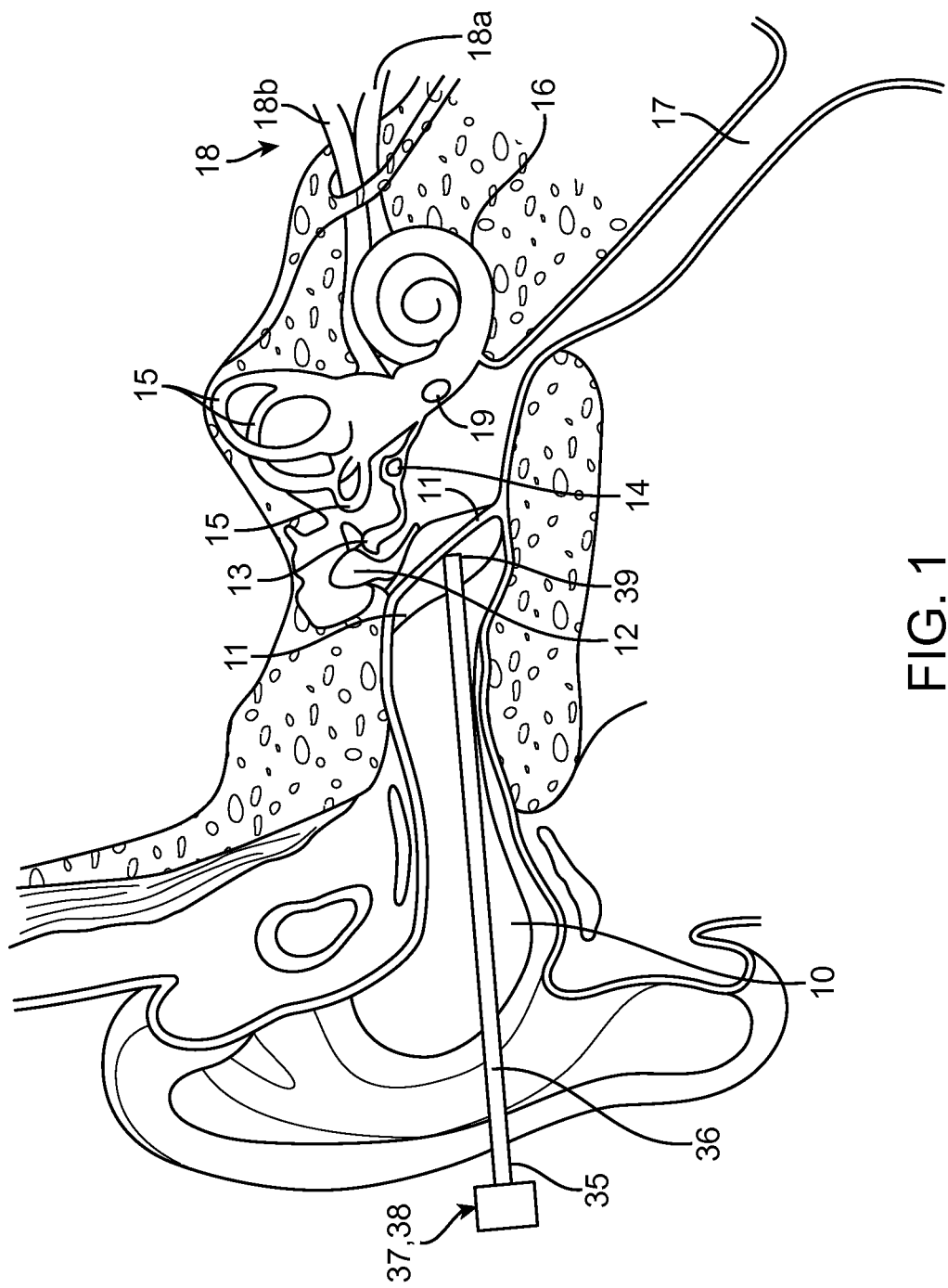
FIG. 1 illustrates an embodiment of the inner ear delivery system including a delivery sheath that is advanceable in the auditory canal.

Embodiments of the invention provide a system and method for delivery of a therapeutic agent to the various locations in the body. Many embodiments provide system and method for delivery of a therapeutic agent to the inner ear. Particular embodiments provide a system and method for delivery of a therapeutic agent to the inner ear for treatment of various disorders of the inner ear. Such embodiments can be used, for example, to deliver therapeutic agent to the round window membrane of the cochlea. Treatment of any type of inner ear disorder is contemplated. Exemplary disorders which can be treated by embodiments of the invention include, but are not limited to, noise induced hearing loss, cisplatin ototoxicity, radiation ototoxicity, surgical trauma, sudden sensorineural hearing loss and autoimmune inner ear disease. Embodiments of invention contemplate delivery of therapeutic agents at therapeutically effective dosages to various location in the inner ear for delivery such disorders.

Embodiments of the invention also contemplate delivery of therapeutic agents to the inner ear to treat other disorders besides that of the inner ear. For example, by absorption of therapeutic agent from the inner ear into one or more of the cerebrospinal fluid, cerebro-circulation interstitial fluid or lymph fluid. Using such an absorption approach, disorders which may be treated by embodiments of the invention may include various neurological disorders such as epilepsy and other related seizure disorders, multiple sclerosis, Alzheimer's, depression, migraine headaches and other related neurological disorders.

Various inner ear disorders which can be treated by one or more embodiments of the invention will now be described. It should be understood that the disorders described herein are exemplary and other inner ear disorders are also contemplated. For each disorder, embodiments of the invention can be used to delivery therapeutically effective dose of therapeutic agent for treatment of the particular disorder for example, one or more corticosteroids for the treatment of noise induced hearing loss. Therapeutically effective doses of these and other therapeutic agents described herein can be determined using known dosage regimens for such agents and conditions with titrations for one or more of the patient's weight, sex, age and amount of hearing loss. Additionally, dose response curves can be developed using methods known in the art (e.g., various pharmaco-kinetic methods) and subsequently used to make further adjustment. For example, dosages may be given to achieve a desired $C_{max}$ either in plasma and/or in the interstitial fluid in and around the inner ear and adjacent tissue. Also, in specific embodiments dosages of a particular therapeutic agent may be adjusted by measuring various aspects of the patient's hearing before and after administration of the therapeutic agents and then determining for example, a dosage which provides for a selected amount of improvement in one or more aspects of the patient's hearing (e.g., hearing over a particular range of frequencies, hearing when larger amounts of ambient noise are present) Various means known in the art for measuring the patient's hearing can be used, such as the hearing evaluator device described in U.S. Pat. No. 7,016,504, to Shennib. Particular amounts of improvement in hearing can be used to select both an initial dose of therapeutic agent as well as a maintenance dose as well in order to sustain the improvement.

Also is describe herein, in many embodiments, the therapeutic agent is formulated into a therapeutic composition which can include one or more excipients such as gelling agent, preservative, etc. Embodiments of the invention also contemplate adjustment of the dosage depending upon the particular excipient. Further, for embodiments using a therapeutic composition comprising a gel (described in further detail herein), which is delivered to a location in the inner ear (e.g., the round window membrane), so as to elute agent from the gel (e.g., into the surrounding interstitial fluid and/or through the round window membrane), adjustment can be made in the dosage to provide a long term delivery of the therapeutic agent over a period of hours (e.g., 6, 12, 24, 48, 96) or days (1, 2, 3, 4, 7 or longer).

One example of an inner ear disorder which can be treated by one or more embodiments of the invention is noise-induced hearing loss (acute or chronic). Exemplary agents for treatment of noise-induced hearing loss include corticosteroids such as dexamethasone or methylprednisone, antioxidants such as D-methionine, N-acetylcysteine, or caroverine, nerve growth and growth factors such as insulin-like growth factor (IGF-1), neurotrophic factor-3 (NT-3), AM-111 peptide or D-JNKI-1 peptide, and immune-suppressant agents such as cyclosporine A or FK506. The later two compounds can also be used for the treatment of autoimmune related hearing disorders.

Another inner ear disorder which can be treated by embodiments of the invention is cisplatin ototoxicity, a common side effect of cisplatin cancer chemotherapy. Therapeutic agents suitable for treatment of cisplatin ototoxicity include antioxidants such as L-methionine or thiourea, and cisplatin binding compounds such as sodium thiosulfate. Otoxicity due to aminoglycoside or other antibiotic therapy can also be treated with antioxidants, or with corticosteroids such as dexamethasone or methylprednisone.

Still other inner ear disorders which can be treated by embodiments of the invention can include radiation ototoxicity, surgical trauma, sudden sensorineural hearing loss and autoimmune inner ear disease. These disorders can be treated, for example, with corticosteroids such as dexamethasone or methylprednisone. In addition, autoimmune inner ear disease may be treated with methotrexate, either alone or in combination with a corticosteroid.

Referring now to FIG. 1, the ear is depicted with the auditory canal 10, tympanic membrane 11, malleus 12, incus 13, stapes 14, semicircular canals 15, cochlea 16, Eustachian tube 17, and cranial nerve 18, with cochlear 18a and vestibular 18b portions. The drawing also illustrates the approximate boundaries for the middle ear ME and the inner ear IE. The inner ear includes without limitation organs, structures and anatomical features such as the semi-circular canals 15, the cochlea 16, and cranial nerve 18.

Referring now to FIGS. 1-5, various embodiments of the invention provide an inner ear delivery system 30 configured to deliver a therapeutic composition 50 (also referred to herein as therapeutic formulation 50 or therapeutic preparation 50) comprising a therapeutic agent 51 (also referred to herein as active agent 51) to one more locations in the inner ear. Typically, the system will comprise a delivery sheath 35 and cannula 40. Delivery sheath 35 (herein referred to as sheath 35) is configured to be inserted into the auditory canal and includes a lumen 36 for the passage of cannula 40. Cannula 40 includes a lumen 42 for the passage of therapeutic composition 50 to a delivery site DS within the ear including the sites in the inner ear. Suitable material for sheath 35 and cannula 40 can include various medical polymers known in the art including without limitation, polyethylene, PET polyurethane, silicone, PTFE and copolymers thereof as well as various metals such as stainless steel as well as various super-elastic metals such as nitinol and like materials.

According to one or more embodiments, sheath 35 can include a proximal portion 37, which is sized to be finger grippable to allow the doctor or other user to advance, twist and otherwise manipulate sheath 35 within the auditory canal. Proximal portion 37 can also be configured as a stop or other depth control feature 38 to control the insertion depth of cannula 40 within the auditory canal. In or more embodiments, proximal portion 37 can also include a finger-tightenable clamp 38c or like device allowing the doctor to fix the lateral position of cannula 40 within sheath 35. In use, clamp 38c allows the doctor to fix the position of distal end 41' of cannula 40 at a desired location such as the round window in order to more precisely control the delivery of therapeutic composition 50 to a desired delivery site DS such as the round window membrane 19.

Sheath 35 is sized and otherwise configured to be inserted into the auditory canal 10 and directed up to the tympanic membrane 11. The direction toward of sheath 35 toward tympanic membrane 11 can be achieved through the use of a preformed upward bend placed in sheath 35 and/or the use of resilient polymers for sheath 35 allowing the medical professional to manually manipulate sheath 35 upward toward tympanic membrane 11. Cannula 40 is sized and otherwise configured to be inserted and advanced through sheath 35 to reach a target site TS in the inner ear. Cannula 40 has a proximal end 40p which may be coupled to a fitting 48 for coupling the cannula to one or more fluid delivery devices 49 (e.g., syringe, pump, etc). It also includes a distal tip 41 (having a distal end 41') configured to pierce the tympanic membrane 11. According to one or more embodiments, this can achieved by configuring distal tip 41 to have a pointed, beveled or otherwise tapered shape. Distal tip 41 may include the last several mms or so of cannula 40 and includes a distal end 41'. While tip 41 is configured to pierce the tympanic membrane 11, according to one or more embodiments, tip 41 can also be configured to otherwise minimize any additional trauma or injury to the tympanic membrane (in addition to piercing of the membrane, e.g., the creation of a flap or excessive tear in the membrane) or other location in the inner ear including the round window membrane 19. Such atraumatic configurations for tip 41 can be achieved through the use of lubricious materials and/or coatings for tip 41 or other portion of cannula 40 to minimize any frictional forces between the tip 41 and the tympanic membrane. Suitable lubricious coatings and materials for tip 41 can include, silicone, PTFE and like materials.

Figure 8A:
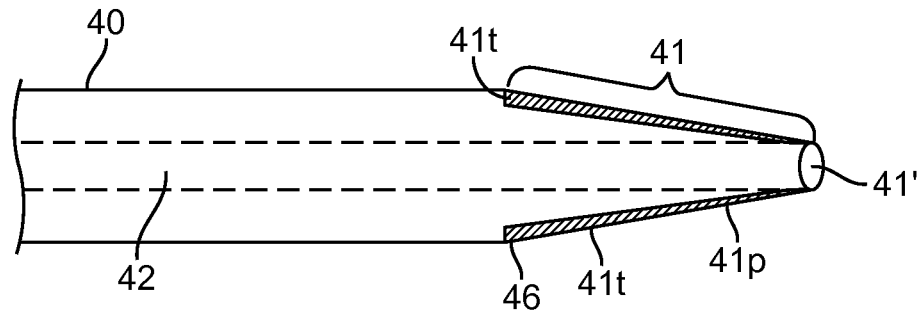
FIGS. 8*a*-8*c* illustrate an embodiment of a cannula distal tip configured to pierce the tympanic membrane but then become substantially atraumatic upon contact with fluid.
Figure 8B:
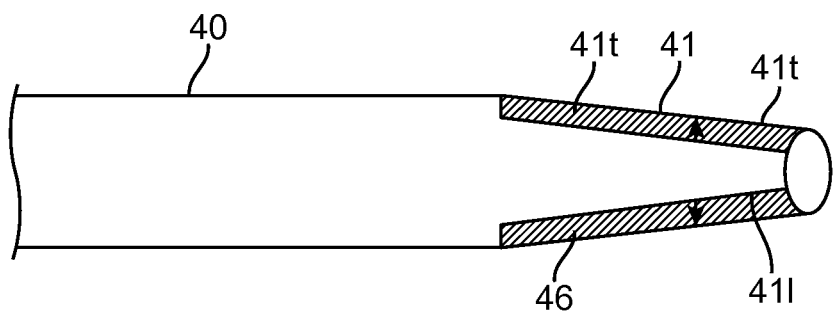
Figure 8C:
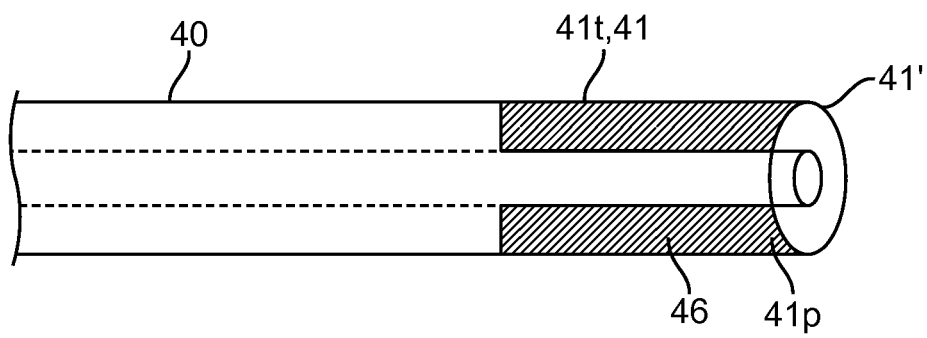

In particular embodiments, distal tip 41 can be configured to be able to penetrate tympanic membrane 11, but at then non-tissue penetrating or otherwise atraumatic to round window membrane 19. Embodiments of the invention contemplate several different approaches for achieving this result. In a preferred embodiment shown in FIGS. 8*a*-8*c*, at least a portion 41*t* of distal tip 41 can comprise a transformable material 46 such as a hydrogel which swells or otherwise transforms upon contact with fluid, such as the fluid in the inner ear (e.g., the perilymph) to transform distal tip 41 into a non-tissue penetrating configuration and/or otherwise atraumatic to the round window membrane. For embodiments having a pointed or beveled distal tip 41*p*, portion 41*t* swells to substantially eliminate the point or bevel as shown in FIGS. 8*b* and 8*c*. Other fluid (e.g., aqueous) swellable materials besides hydrogels are also contemplated. Portion 41*t* can also be configured to swell or otherwise transform to an atraumatic form upon contact with liquid based form of therapeutic composition 50 or other fluid (e.g., saline or other aqueous based fluid) that is injected or otherwise delivered through lumen 42. Alternative embodiments contemplate other approaches for transforming distal tip 41 into an atraumatic configuration after piercing the tympanic membrane. In one such alternative approach (not shown), the distal tip 41 can be configured to turn in on itself or flair (i.e., to invert) after piercing the tympanic membrane so as to eliminate any point or bevel in the tip. In another related approach, the distal tip 41 can be configured to flare out (i.e., to evert) after piercing the tympanic membrane so as to assume an atraumatic shape (e.g., bell shaped). Such inverting or everting shapes can be achieved through the use of transformable materials such as hydrogel which transforms upon contact with water, and/or the use of shape memory materials which transform to a preformed memory shape upon increase in temperature above a temperature known as the transition temperature which can be configured to be at or slightly below body temperature (e.g., in the range of 92 to 98° F.). Suitable shape memory materials which can make this transformation include nitinol (e.g., nickel titanium alloys) as is known in the art.

In various embodiments using ultrasonic and/or fluoroscopic image guidance for system 30, one or both of sheath 35 and cannula 40 may be formed from radio-opaque or echogenic materials and may include distinct markers 39 and 43 made of such materials (e.g., proximal, distal and midpoint markers). Markers 43 made of other materials which are visible under other forms of medical imaging modality are also contemplated. For, example markers 43 may be made of material which is readily visible using an ear-based endoscope device. This can be achieved by a selecting a color for the marker which has high contrast verses the tissue in the inner ear and/or the color of cannula 40.

In particular embodiments, the distal tip 41 of cannula 40 can include one or more markers 43 having a diameter 43*d* sized so as to allow the doctor to use the marker(s) as a gauge 44 to size the diameter of the drop 52 of therapeutic agent preparation 50 delivered to the round window membrane 19 or other delivery site DS. Gauge 44 is also referred to herein as a gauge marker 44. Typically, gauge marker 44 will have a rectangular shape with the width of the rectangle corresponding to the desired drop size diameter. Other drop size measurement means 45 in addition to gauge 44 are also contemplated for use in measurement of drop 52. Such measurement means 45 may include for example a radio-opaque/echogenic band (not shown) attached distal tip 41, as well one or more sensors (not shown) attached to the distal tip 41 (on the inside or outside) which provide an output correlated to the diameter of drop 52. Such sensors may include, for example, various acoustic sensors (e.g., which may include an emitter and detector), optical (which may include an emitter and detector) or electrical sensors which may resistance/impedance sensors.

Figure 2:
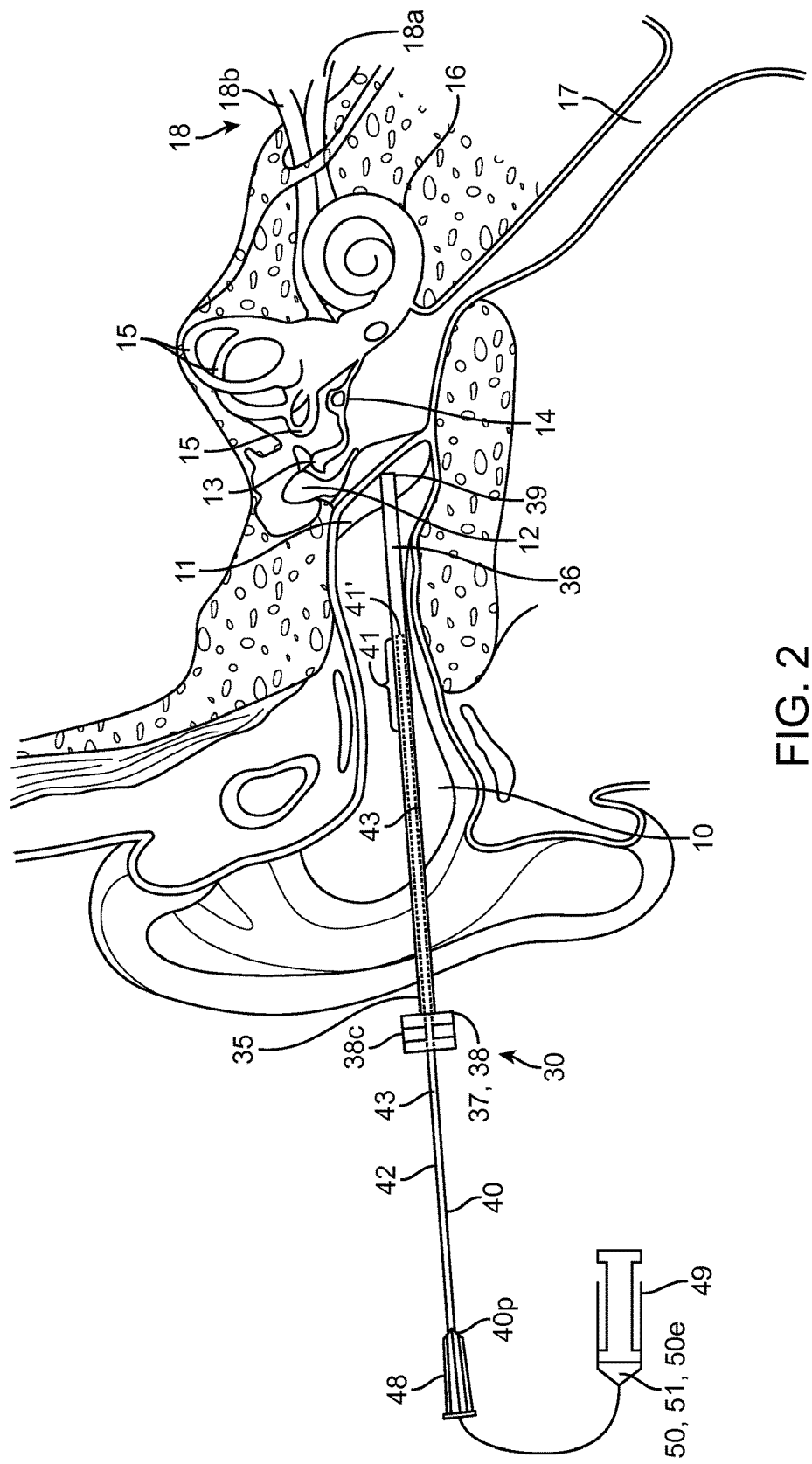
FIG. 2 illustrates an embodiment of the delivery system including the delivery sheath and delivery cannula and advancement of the delivery cannula through the delivery sheath.
Figure 3:
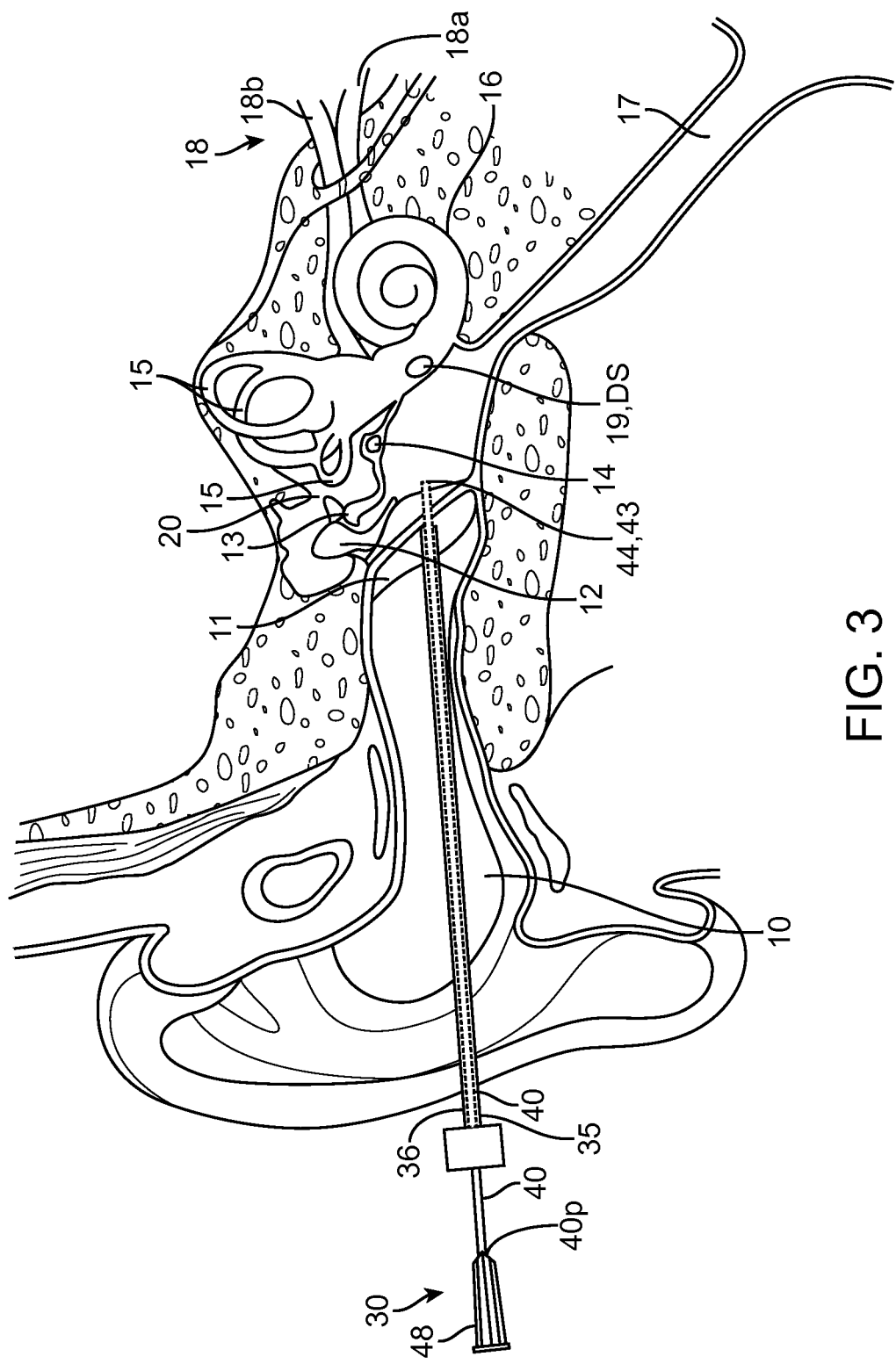
FIG. 3 illustrates advancement of the cannula to penetrate the tympanic membrane.
Figure 4:
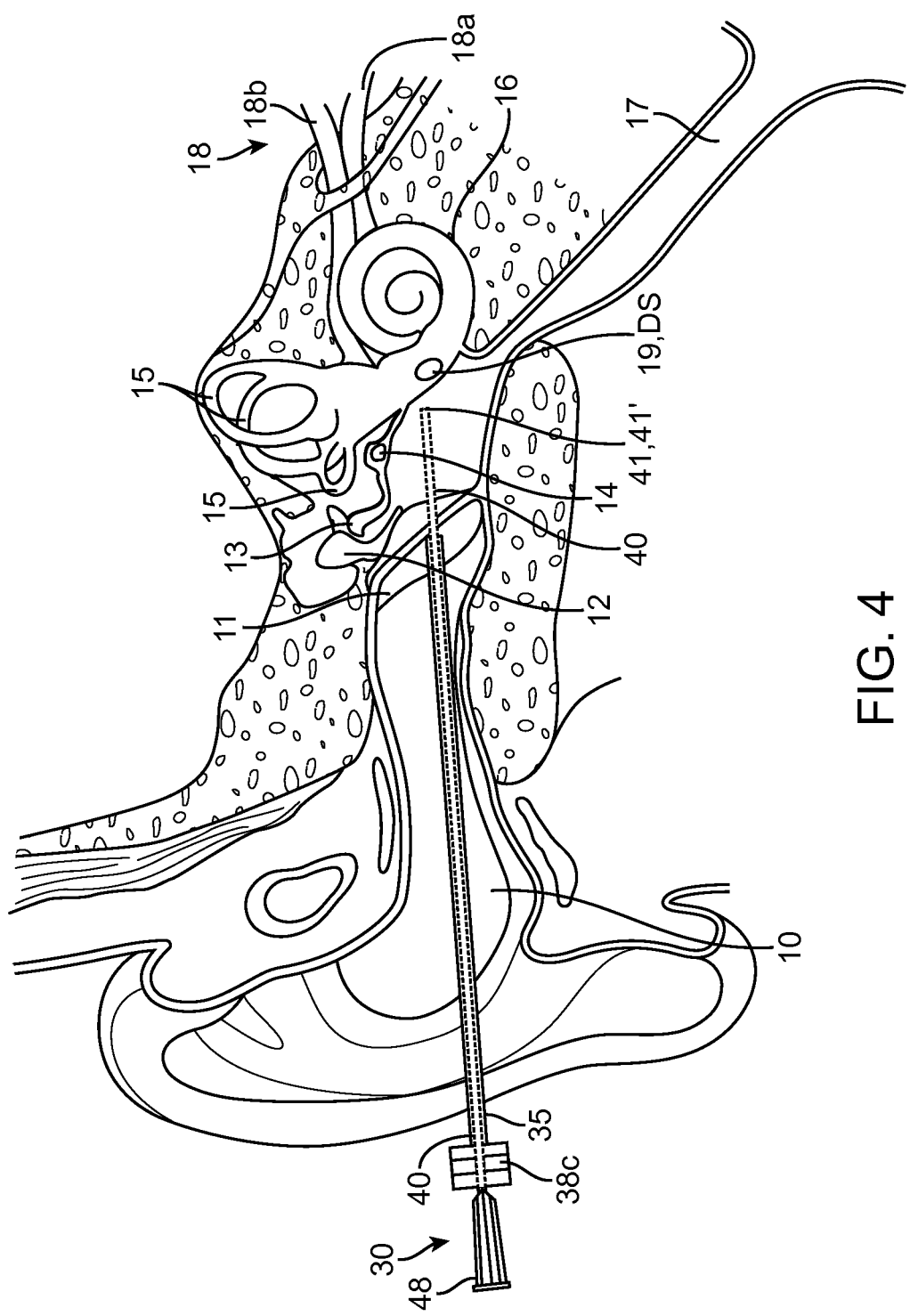
FIG. 4 illustrates advancement of the cannula to position the distal tip of the cannula adjacent the round window membrane of the inner ear.
Figure 5:
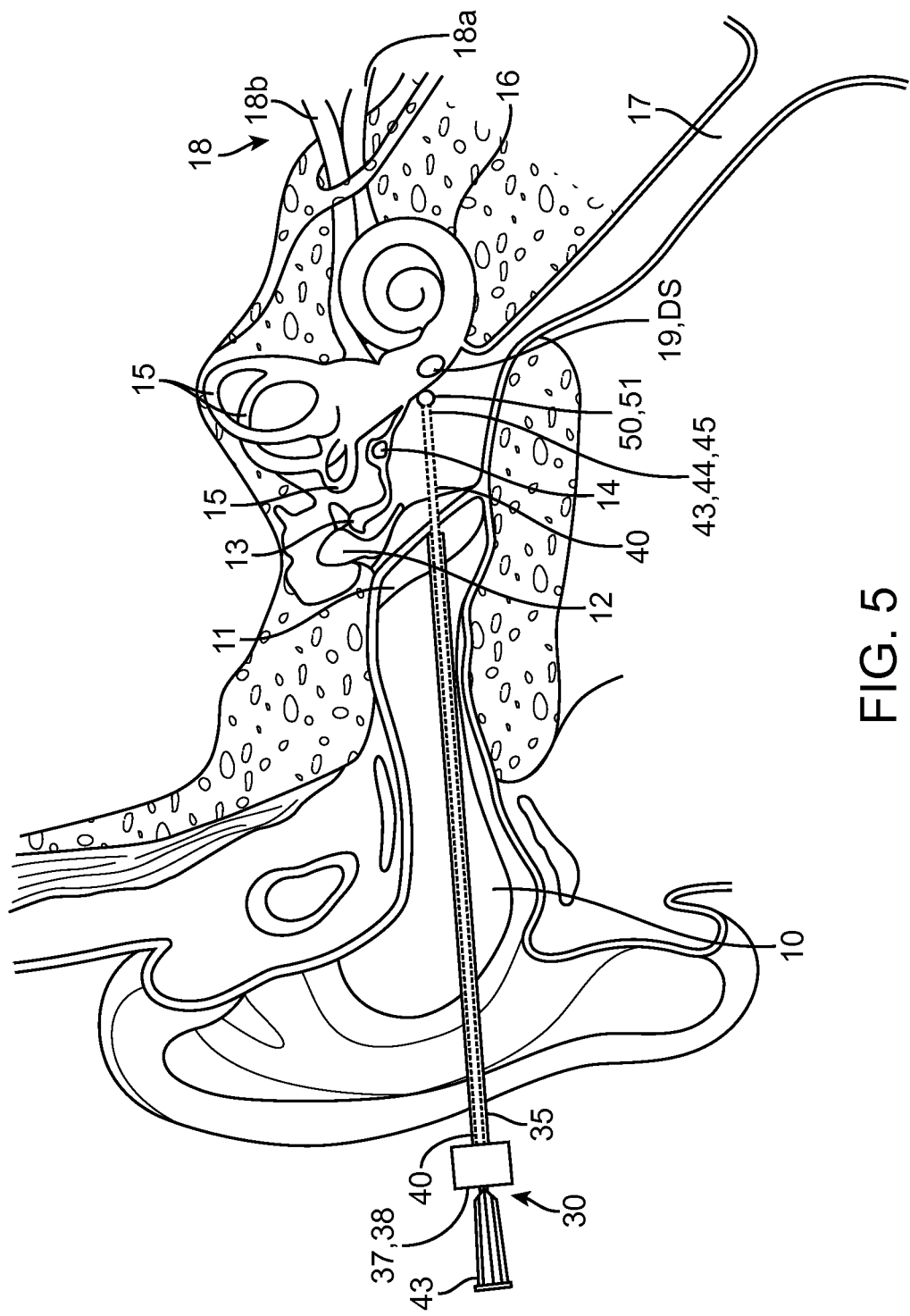
FIG. 5 illustrates delivery of a therapeutic composition to the round window membrane through the cannula.
Figure 6:
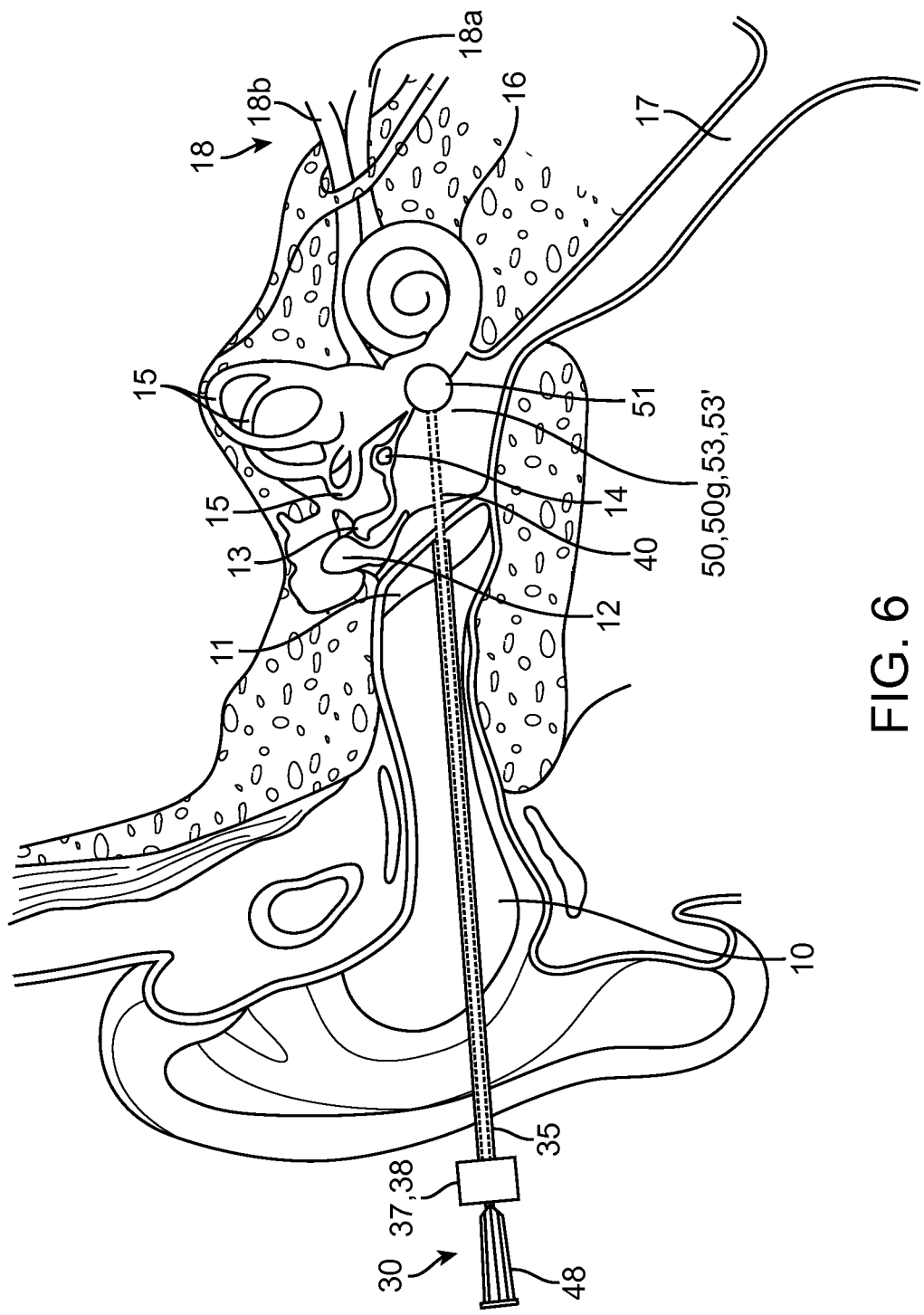
FIG. 6 illustrates delivery of a gel-form therapeutic composition to the round window membrane through the cannula.
Figure 7:
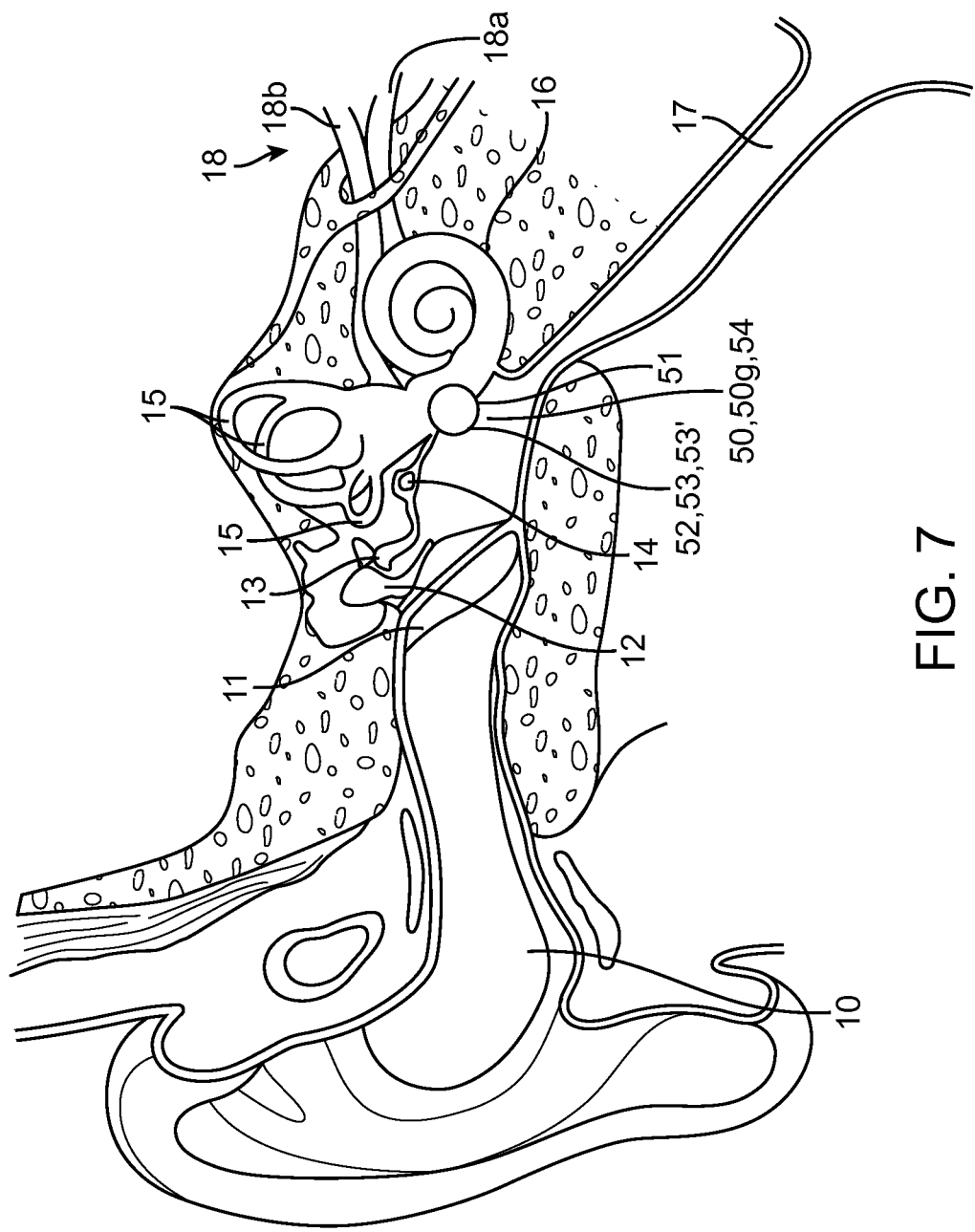
FIG. 7 the delivered drop of gel-form therapeutic composition adhered to the round window, with cannula and sheath withdrawn.

Referring now to FIGS. 2-7 exemplary embodiments of methods for using embodiments of system 30 for delivery a therapeutic composition 50 to a delivery site in the inner ear will now be described. Such embodiments are particularly useful for treating various disorders of the inner ear, but may also be used for the delivery of therapeutic agents for the treatment of other conditions as well, for example, various neurological conditions. As shown in FIG. 1 sheath 35 is inserted into the auditory canal 10 and directed up to the tympanic membrane 11. As discussed below, this may done using an endoscopic viewing device or using one more medical imaging modalities known in the art (e.g., ultrasound etc.) The tympanic membrane is generally anesthetized prior to introduction of the delivery sheath 35 using methods known in the art. As shown in FIG. 2, cannula 40 is then inserted into the delivery sheath 35. FIG. 3 illustrates that insertion of the cannula 40 continues until the end of the cannula 40 pierces the tympanic membrane 11 and continues into the middle ear 20. Insertion of the cannula 40 continues until the distal end 41' is adjacent to the round window membrane 19 of the cochlea 16, as shown in FIG. 4. It should be appreciated that the round window membrane 19 is an exemplary delivery site DS and other delivery sites in the inner ear may also be selected. Once distal end 41' is situated next to the round window membrane 19, a therapeutic composition 50 is injected through the delivery lumen 42, as shown in FIG. 5. FIG. 6 illustrates that injection of therapeutic composition 50 continues until a sufficient amount of composition 50 has been introduced so as to provide a therapeutically effective amount of therapeutic agent 51 for the treatment of a selected condition or condition(s). This figure also illustrates the delivery of therapeutic composition 50 which has a gel form 50*g* upon delivery to round window 19 or other delivery site DS. The cannula 40 and delivery sheath 35 may then be withdrawn from the ear, with a drop 52 of the therapeutic composition 50 in place at the round window membrane 19, as shown in FIG. 7.

The above procedure is typically performed by an ENT specialist or an otolaryngologist. In many embodiments, it may be performed using various using various ear-based endoscopes devices (herein an endoscope) known in the art and in these and related embodiments, sheath 35 and cannula 40 may be sized and otherwise configured to pass through the endoscope. In other embodiments, the procedure may also be done under one or more medical imaging modalities known in the art including for example, ultrasound or fluoroscopy.

Figure 9A:
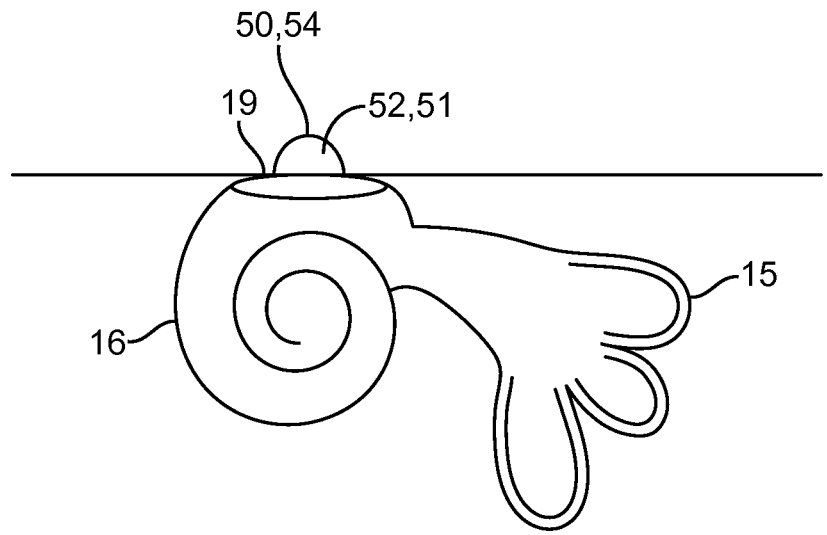
FIGS. 9*a*-9*b* illustrate diffusion of therapeutic agent across the round window membrane to fluid inside the cochlea from a drop of therapeutic formulation placed on the membrane, as well as outward diffusion (e.g., elution) of therapeutic agent from the drop. The figures also illustrate use of the drop of therapeutic agent as a reservoir or drug depot for the long term delivery of therapeutic agent to locations in the inner ear.
Figure 9B:
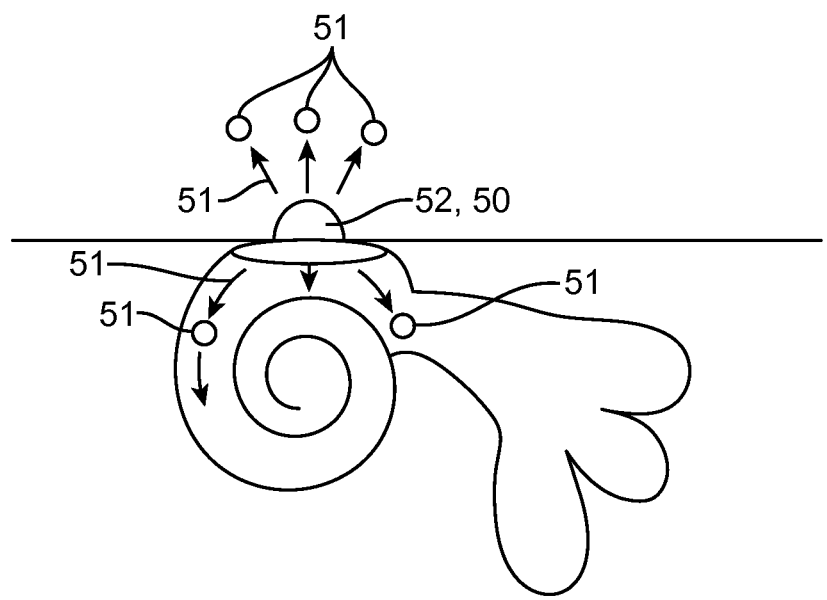

As discussed herein, in many embodiments, the therapeutic agent 51 is delivered in the form of a therapeutic agent composition 50 comprising the therapeutic agent 51 and one or more excipients 50*e* such as carriers, preservatives, antioxidants, etc. Referring now to FIGS. 9*a* and 9*b*, according to one or more embodiments, therapeutic composition 50 can be configured to adhere to the round window membrane 19 (e.g., in the form of a drop 52 of preparation placed on the membrane using cannula 40) to allow for diffusion of therapeutic agent 51 across the round window membrane 19 and into fluid within the inner ear (e.g. the perilymph) so as to reach one or more locations in the inner ear such as cochlea 16. Drop 52 may also be placed on membrane 19 to allow for elution (e.g., release of agent 51 by outward diffusion from the drop 52) of therapeutic agent 51 from the drop to other locations within the inner ear as well. Such adherence and/or diffusion can be achieved by selection of the surface tension, viscosity, or other rheological property of formulation 50 as well as the size of the drop 52 of formulation 50 placed at delivery site DS. As is discussed in further detail herein, in particular embodiments, drop 52 (or other form of preparation 50) so placed at membrane 19 can be configured as a drug depot 54 to provide for the long term release of agent 51 to locations in inner ear such as the cochlea. In these and related embodiments preparation 50 can be formulated from one or more biodegradable carrier agents 53 to allow the drop 52 to remain on membrane 19 or other surface in the inner ear for an extended period of time (as is discussed below) before breaking down through the process of biodegradation (e.g., by hydrolysis). Suitable carrier agents can include, for example, PLA and PGLA as is discussed in great detail herein. In particular embodiments, the carrier agents and other exicipients making up formulation 50 can be selected and included in amounts to minimize the effect of drop 52 on the patient's hearing. Such reduced effect on the patient's hearing can be achieved by carrier agents having lower molecular weights, lower viscosity and/or lower amounts of cross linking.

In or more embodiments wherein therapeutic agent preparation 50 is delivered to the surface of the round window so as to adhere to and/or be absorbed through the round window membrane 19, the amount of therapeutic composition 50 delivered to the window membrane 19 can be selected as to provide for a therapeutically effective amount of therapeutic agent 51 which: i) diffuses through the round window membrane 19 to reach the cochea 16 or other inner ear structure, and/or elutes from drop 52 to reach one or more other locations within the inner ear. Further, in either case, the amount of therapeutic composition 50 delivered to round window membrane from drop 52 can be configured to provide for the long term release of therapeutically effective amounts of therapeutic agent 51 from drop 52. The long term release of therapeutic agent 51 from drop 52 can be configured to be over a period of hours (about about 4, 8, 12, 18, 24, etc.) or days (e.g., about 1, 2, 3, 5, 7, 14, days etc) In this way, only a single dose of therapeutic agent preparation 50 need be provided to the round window membrane (or other location) so as to provide for a therapeutically effective delivery of the agent 51 over a period of hours or days.). In particular embodiments, the release period can be being determined for example, by the selection of the gelling agent (e.g., collagen) 53' or other carrier agent 53, it's properties (e.g., the amount of cross linking) as well as the amount of therapeutic agent in drop 52. In particular embodiments, gelling agents 53' or other carrier agents 53 having greater amounts of crosslinking can be used to achieve longer release profiles. Such results can also be achieved through the use of a gelling agent 53' or other excipients 50e known in the art having a chemical affinity for the particular therapeutic agent 51.

Figure 10A:
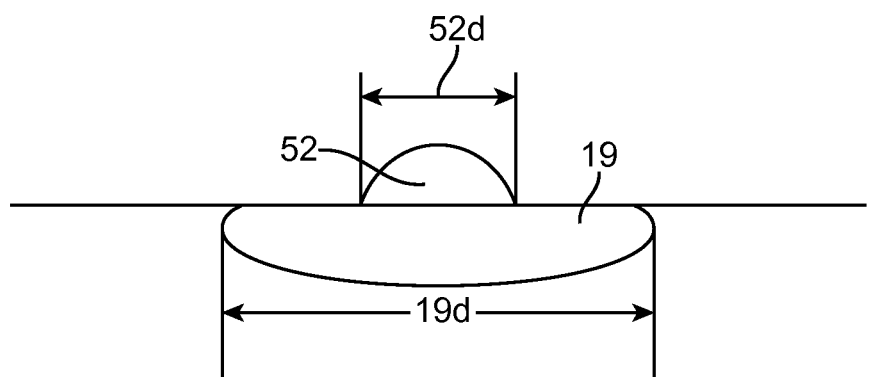
FIGS. 10*a*-10*c* illustrate embodiments of a drop of therapeutic formulation placed in the ear and configured so as to not interfere with patients hearing.
Figure 10B:
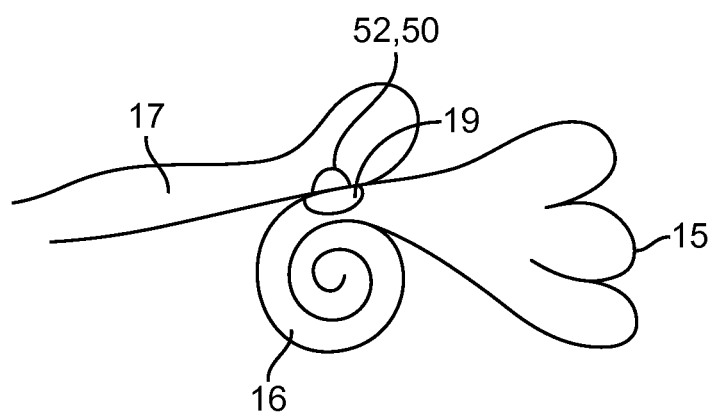
Figure 10C:
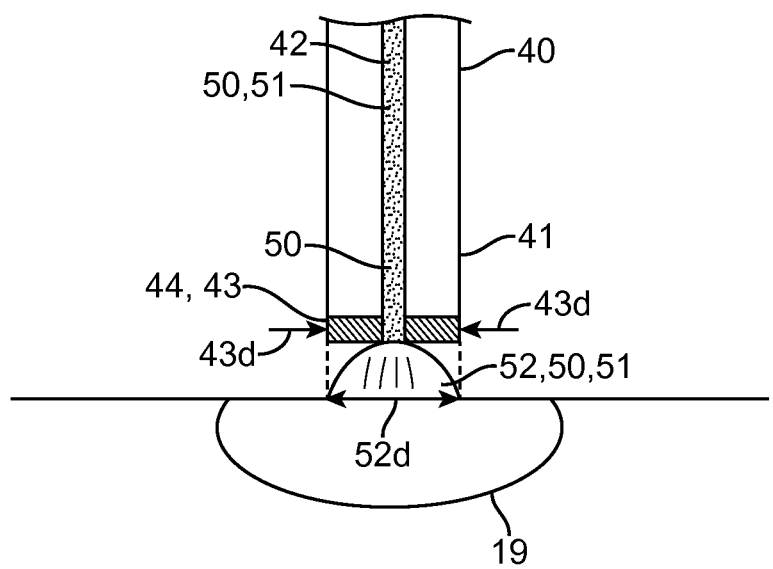

Referring now to FIGS. 10a-10c, according to one or more embodiments, the size of the drop 52 (or other shape) of therapeutic formulation 50 positioned on round window membrane 19 (or other surface in the patient's inner ear) can be selected so as to not substantially interfere with the patient's hearing process. As used herein, the term "substantially interfere with patient's hearing refers" to a decrease in the patient hearing of greater than about 10% (e.g., as measured in sensitivity to a given amplitude in dB), with lower amounts also contemplated. For example, in particular embodiments the drop 52 of formulation 50 does not substantially interfere with the proper functioning of the round window 19. In particular embodiments for achieving this result, the diameter or other major dimension 52d of drop 52 is less than the diameter 19d of round window 19 as shown in FIG. 10a In particular embodiments, diameter 19 can be less than about, 50, 30, 25, 10 or 5% of diameter 19d. Since the average diameter of round the window is about 2.5 mm, in particular embodiments, the diameter of 52d of drop 52 may correspond to diameters of about 1.25, 0.83, 0.63 or 0.12 mm. Also, in one or more embodiments, the size and position of the drop 52 of formulation 50 can be selected so as to not substantially block the Eustachian tube 17 (shown in FIG. 10b) or cause irritation of the round window membrane 19. As used herein, the term "substantially block the Eustachian tube 17" refers to a blockage of greater than about 10%, with lower amounts of blockage also contemplated. The size of drop 52 of therapeutic preparation 50 can be controlled to meet one or more of these objectives by selection of one or more of the internal diameter of cannula 40, the surface tension of the material comprising cannula 40, the surface tension of therapeutic preparation 50. In preferred embodiments, drop size as determined by the diameter 52d of or major dimension of drop 52 is controlled using one or more gauge markers 44 as is shown in FIG. 10c. Various tests can be done using drops size measurement methods known in the art (e.g., using a goniometer) and combinations of the previously listed parameters to determine the drop size and/or range of drop sizes produced by such combinations and one or more of the parameters adjusted accordingly to achieve the desired drop size.

Various embodiments of the invention contemplate several other methods for controlling the drop size of therapeutic agent preparation 50 to meet the desired criteria. In one or more embodiments, the size of drop 50 can be controlled using a controllable fluid delivery device 49 such as a metered pump, syringe or other like device that is fluidically coupled to the proximal end 40p of cannula 40 by means of fitting 48 (e.g., such as luer lock fitting). In addition, to controlling drop size, such devices can also be configured to also control the volume, mass or other parameter corresponding to an amount of therapeutic agent placed on the round window membrane (or other location) and/or the effect of that amount on the round window function. In other embodiments, the drop size of therapeutic agent preparation 50 can be monitored visually using an endoscope and/or various medical imaging modalities, (e.g., ultrasound, fluoroscopy, etc.). In the later embodiments, therapeutic agent preparation 50 may include echogenic and/or radio-opaque materials (described herein) and cannula 40 echogenic and/or radio-opaque markers 41 allowing the doctor to visually size the drop 52 using the imaging modality. This can be done by measurement of size of drop 52 from the imaging modality and/or use of markers 43 including gauge markers 44. In still other embodiments, drop size 52 can be controlled by monitoring the patient's hearing while the therapeutic agent preparation 50 is being delivered (this can be done in conjunction with other approaches described above, e.g., visually monitoring of the drop size and/or use of controllable fluid delivery device). Various hearing monitoring test methods and devices can be used. One example of a suitable hearing monitoring device and associated tests which can be used include a personal hearing evaluator described in U.S. Pat. No. 7,016,504, to Shennib which is fully incorporated by reference herein for all purposes. Such a device can be used to deliver multilevel stimuli and multiple frequencies to evaluate hearing. Various monoaural hearing evaluations can also be done as is known in the art. Also, in this and related embodiments, the response or the ear in which system 30 is placed can be compared to the opposite ear which is used as a control. Various EEG and related methods may be used to quantitatively monitor the patient's hearing using the hearing evaluator described by Shennib or another hearing evaluator and/or methodology known in the art.

In many embodiments, the therapeutic composition 50 can be formulated as a gel 50g as is shown in the embodiments of FIGS. 6 and 7. This can be accomplished using one or more gelling agents 53' known in the art. Suitable gelling agents 53' can include for example, collagen, gelatin, xantham gum, sodium alginate, carrageenan and carboxymethylcellulose and combinations thereof. In particular embodiments, gel 50g can comprise a thixotropic gel or carrier material. By "thixotropic" it is meant that the material is gel-like (e.g., higher viscosity) under static conditions, but has liquid-like properties (e.g., lower viscosity) when shaken, agitated, or otherwise subjected to shear stress, e.g., when being delivered through a lumen such as the lumen 42 of cannula 40. Such thixotropic materials allow the composition 50 to be delivered by cannula 40 (or other conduit, e.g., a hypotube) to a delivery site DS in the inner ear in liquid form and then become a gel again at the site so as to provide for localized drug delivery of the therapeutic agent to tissue at the delivery site DS. The gel 50g, in essence, functions as a drug depot or reservoir 54 allowing for prolonged delivery of the therapeutic agent 51 to tissue in the inner ear. Any number of thixotropic agents known in the art can be used, Exemplary thixotropic gels are described in U.S. Pat. No. 7,820,202; US 2006/0193877; U.S. Pat. No. 5,212,162; and elsewhere in the patent and medical literature. The full disclosures of these patents and patent publications are incorporated herein by reference for all purposes.

In one or more embodiments, the rheological properties of gel 50g can be selected to control the rate of release of one or more therapeutic agents 51 from the gel. Such properties can include, for example: viscosity (e.g., static and dynamic viscosity), surface tension, molecular weight and the amount of cross linking of the gel. In specific embodiments, higher viscosity gels can be selected for slower rates of release and visa versa. In specific embodiments, the gel 50g can comprise a first and second gelling agent 53' having a faster and slower rate of release of therapeutic agent 51 due to differences in viscosity or other property of each agent. In use, such embodiments allow for both an immediate and longer term release of one or more therapeutic agents 51 from the gel 50g. Additionally, properties of the therapeutic agent 51, such as molecular weight and charge, can be taken into account when preparing gel formation 50g as they may effect the rate of release of the gel. For example, therapeutic agents 51 having higher molecular weights can be selected to achieve longer periods of drug release and visa versa. Also, according to one or more embodiments, longer periods of drug release can achieved by selecting therapeutic agents and gels (or other carrier agents 53) having opposite charges so as to at least partially retain the therapeutic agent by ionic attraction. In alternative embodiment, faster rates of release of therapeutic agent can be achieved by using of charged therapeutic agents 51 in formulation and 50 then applying a current to drop 52 of formulation 50 delivered to the round membrane which has the same charge as the therapeutic agent so as to repel the therapeutic agent through the round window by means of electrostatic repulsion and iontophoresis. Further description of the use of iontophoresis devices and methods for delivering therapeutic agents may be found in U.S. Pat. No. 8,190,252 to Imran which is fully incorporated herein by reference for all purposes. According to one or more embodiments, electrical current may be applied to the drop 52 by means of an embodiment of cannula 40 that is configured to be coupled to a current source and/or by use of RF energy which is transmitted to the drop 52 by means of an external RF energy source, such as an RF transmitter chip or an RF transmitter chip which is positioned on the tip of canulla 40, or sheath 35 or other device positioned within the auditory canal and/or into the inner ear.

In some embodiments, the desired drug release profile of therapeutic composition 50 can be achieved through appropriate selection of the gelling or other carrier agents 53 such as PLA, PLGA and blends of PLA/PLGA. For example, a drug release half-life of up to 6 months can be achieved with an appropriate PLA/PLGA blend. Citric acid based polymers can also be used to produce a therapeutic drug formulation having good sustained release drug depot properties.

In addition to delivery of therapeutic agents 51 for treatment of a particular inner ear or other disorder, various embodiments of the invention may include one or more anti-inflammatory agents known in the art so as to minimize any inflammation to the inner ear caused by the insertion of cannula 40 through the tympanic membrane and into the middle ear. Suitable anti-inflammatory agents are listed, for example, in US Patent Publication number 2007/0100318, the full disclosure of which is incorporated herein by reference for all purposes.

The foregoing description of various embodiments of the invention has been presented for purposes of illustration and description. It is not intended to limit the invention to the precise forms disclosed. Many modifications, variations and refinements will be apparent to practitioners skilled in the art. For example, one more embodiments of system 30 may be sized or otherwise configured for various pediatric and/or neonatal applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A method for treating a disorder of the inner ear of a patient using a therapeutic composition comprising a therapeutic agent, the method comprising:
   introducing a delivery sheath through the auditory canal to be positioned adjacent to the tympanic membrane;
   introducing a cannula through the delivery sheath to pierce the tympanic membrane and then be advanced to position a distal end of the cannula adjacent a tissue surface comprising the round window membrane, the composition configured to adhere to the tissue surface of the round window membrane for an extended period of time;

delivering a single drop of a therapeutically effective amount of the therapeutic composition through the cannula to the tissue surface such that the composition adheres to the tissue surface for the extended period of time, the single drop of the therapeutic composition having a drop size which does not significantly affect the function of the round window such that the patient's hearing is not reduced by more than 10%;

wherein the drop has a major diameter measured when placed on the round window which is equal or less than about 1.25 mm, and wherein the drop size of therapeutic agent is measured using a gauge positioned on a distal portion of the cannula, the gauge being visible under a medical imaging modality; and delivering the therapeutic agent from the therapeutic composition on the tissue surface to the inner ear.

2. The method of claim 1, wherein the therapeutic agent is configured to diffuse through the tissue surface to deliver the therapeutic agent to the inner ear.

3. The method of claim 2, wherein the therapeutic agent diffuses through the tissue surface to provide for a long term release of therapeutic agent to the inner ear.

4. The method of claim 3, wherein the long term release of therapeutic agent occurs over a period up to about 24 hours.

5. The method of claim 3, wherein the long term release of therapeutic agent occurs over a period up to about 96 hours.

6. The method of claim 1 wherein the major diameter of the drop is equal or less than about 0.63 mm.

7. The method of claim 1, wherein the drop size of therapeutic agent is controlled using a rheological property of the therapeutic composition including at least one of viscosity or surface tension of the composition.

8. The method of claim 1, wherein the therapeutic composition comprises a thixotropic material which allows the therapeutic composition to be delivered through the cannula in a liquid form and then convert to a gel form when delivered to the tissue surface.

9. The method of claim 8, wherein the therapeutic composition comprises at least one of PLA, PLGA, a PLA/PLGA blend or collagen.

10. The method of claim 1, wherein the therapeutic composition comprises a corticosteroid.

11. The method of claim 10, wherein the corticosteroid is delivered to treat noise induced treat hearing loss.

12. The method of claim 10, wherein the therapeutic composition comprises dexamethasone.

13. The method of claim 10, wherein the therapeutic composition comprises methylprednisone.

14. The method of claim 1, wherein the therapeutic composition comprises an antioxidant.

15. The method of claim 14, wherein the antioxidant is delivered to treat cisplatin ototoxicity.

16. The method of claim 14, wherein the antioxidant is selected from the group consisting of D-methionine, N-acetylcysteine, and thiourea.

17. The method of claim 1, wherein the therapeutic composition comprises a growth factor or nerve growth factor.

18. The method of claim 1, wherein the therapeutic composition comprises an immune-suppressant agent.

19. The method of claim 1, wherein the extended period of time is from about 4 hours to 14 days.

20. A method for treating a disorder of the inner ear of a patient using a therapeutic composition comprising a therapeutic agent, the method comprising:

introducing a delivery sheath through the auditory canal to be positioned adjacent to the tympanic membrane;

introducing a cannula through the delivery sheath to pierce the tympanic membrane and then be advanced to position a distal end of the cannula adjacent a tissue surface in or near the round window to allow the therapeutic composition to be delivered to a surface on the round window, the composition configured to adhere to the tissue surface for an extended period of time;

delivering a therapeutically effective amount of the therapeutic composition through the cannula to the tissue surface such that the composition adheres to the tissue surface for the extended period of time, the delivered amount of therapeutic agent comprising a drop of the therapeutic composition having a drop size which does not significantly affect the function of the round window such that patient's hearing is not reduced by more than 10%, wherein the drop has a major diameter measured when placed on the round window which is equal or less than about 1.25 mm, and wherein the drop size of therapeutic agent is measured using a gauge positioned on a distal portion of the cannula, the gauge being visible under a medical imaging modality; and delivering the therapeutic agent from the therapeutic composition on the tissue surface on the round window to the inner ear.

21. A method for treating a disorder of the inner ear of a patient using a therapeutic composition comprising a therapeutic agent, the method comprising:

introducing a delivery sheath through the auditory canal to be positioned adjacent to the tympanic membrane;

introducing a cannula through the delivery sheath to pierce the tympanic membrane, the cannula having a gauge positioned on a distal portion of the cannula, the gauge configured to measure a drop size of a therapeutic composition delivered from the cannula tip to a tissue surface on the inner ear;

advancing the cannula to position a distal end of the cannula adjacent a tissue surface in or near the round window to allow the therapeutic composition to be delivered to a surface on the round window; the composition configured to adhere to the tissue surface for an extended period of time;

delivering a single drop of a therapeutically effective amount of the therapeutic composition through the cannula to the tissue surface, said single drop having a size selected to adhere to the tissue surface for the extended period of time; wherein the gauge is used to control a drop size of the therapeutic composition delivered to the tissue surface;

wherein the drop has a major diameter measured when placed on the round window which is equal or less than about 1.25 mm, and wherein the drop size of therapeutic agent is measured using a gauge positioned on a distal portion of the cannula, the gauge being visible under a medical imaging modality; and delivering the therapeutic agent from the therapeutic composition on the tissue surface on or adjacent the round window to the inner ear.

22. A method for treating a disorder of the inner ear of a patient using a therapeutic composition comprising a therapeutic agent, the method comprising:

introducing a delivery sheath through the auditory canal to be positioned adjacent to the tympanic membrane;

introducing a cannula through the delivery sheath to pierce the tympanic membrane and then be advanced to position a distal end of the cannula adjacent a tissue surface to allow the therapeutic composition to be delivered to the tissue surface, the tissue surface being on the round window, the composition configured to adhere to the tissue surface of the inner ear for an extended period of time;

delivering a single drop of a therapeutically effective amount of the therapeutic composition through the cannula to the tissue surface such that the composition adheres to the tissue surface for the extended period of time, the delivered amount of therapeutic agent having a drop size which does not significantly affect the function of the round window such that the patient's hearing is not reduced by more than 10%;

wherein the drop has a major diameter measured when placed on the round window which is equal or less than about 1.25 mm, and wherein the drop size of therapeutic agent is measured using a gauge positioned on a distal portion of the cannula, the gauge being visible under a medical imaging modality;

delivering the therapeutic agent from the therapeutic composition on the tissue surface to the inner ear; and wherein the therapeutic composition antioxidant is delivered to treat cisplatin ototoxicity.

* * * * *